US00PP26973P3

(12) United States Plant Patent
Leis et al.

(10) Patent No.: US PP26,973 P3
(45) Date of Patent: Jul. 26, 2016

(54) APPLE TREE NAMED 'CIV323'

(50) Latin Name: ***Malus domestica* Mill.**
Varietal Denomination: CIV323

(71) Applicant: C.I.V. - CONSORZIO ITALIANO VIVAISTI - SOCIETÀ CONSORTILE A R.L., Comacchio FE (IT)

(72) Inventors: Michelangelo Leis, Ferrara (IT); Alessio Martinelli, Ferrara (IT); Francesco Tagliani, Argenta (IT); Gianfranco Castagnoli, Quingentole (IT)

(73) Assignee: C.I.V.—Consorzio Italiano Vivaisti—Società Consortile A R.L., Comacchio FE (IT)

( * ) Notice: Subject to any disclaimer, the term of this patent is extended or adjusted under 35 U.S.C. 154(b) by 216 days.

(21) Appl. No.: 13/986,177

(22) Filed: Apr. 9, 2013

(65) Prior Publication Data

US 2013/0269069 P1 Oct. 10, 2013

(30) Foreign Application Priority Data

Apr. 10, 2012 (QZ) ..... PBR 2012/0805

(51) Int. Cl.
*A01H 5/08* (2006.01)

(52) U.S. Cl.
USPC ..... Plt./161
CPC ..... *A01H 5/0875* (2013.01)

(58) Field of Classification Search
USPC ..... Plt./161
CPC ..... A01H 5/0875; A01H 5/08
See application file for complete search history.

(56) References Cited

PUBLICATIONS http://www.braun-apple.com/sorten0.html?&L=2; 2006, 2 pages.*

* cited by examiner

*Primary Examiner* — Kent L Bell
(74) *Attorney, Agent, or Firm* — Foley & Lardner LLP

(57) ABSTRACT

A new and distinct *Malus domestica* Mill. apple tree variety named 'CIV323' particularly characterized by a moderately vigorous tree with open habit. Highly productive with precocious fruit bearing. Resistant to scab. The fruit is red, medium in size with a regular cylindrical shape. The flesh is creamy, fine, crispy and juicy. the flavour is good, with high acid level a good content of sugar. Good storability under ULO-conditions for up to six months.

4 Drawing Sheets

Latin name of the genus and species of the plant claimed: *Malus domestica* Mill.

Variety denomination: 'CIV323'.

PRIORITY CLAIM

This application claims priority to European Community Plant Variety Office Application No. 2012/0805 filed Apr. 10, 2012, the disclosure of which is incorporated by reference herein in its entirety.

BACKGROUND OF THE INVENTION

The present invention relates to a new and distinct variety of apple tree, botanically known as *Malus domestica* Mill. of the Family Rosaceae, and hereinafter referred to by the variety denomination 'CIV323'.

The new *Malus* variety is a product of a planned breeding program conducted by the inventors, Michelangelo Leis, Alessio Martinelli, Francesco Tagliani and Gianfranco Castagnoli in S. Giuseppe di Comacchio (Ferrara), Italy. The objective of the breeding program was to develop new *Malus* varieties with improved production characteristics, high-quality flavour and aroma and sustainability by increasing the tree's natural resistance. The primary objective of the Applicant's research program is to select new apple varieties with natural resistances, in particular to scab.

The new *Malus* variety, 'CIV323', originated from a cross made in a planned, controlled breeding program in S. Giuseppe di Comacchio (Ferrara), Italy. The female parent is the apple variety 'Galaxy' (unpatented). The male parent is an unpatented, proprietary selection denominated 'A3-7'. 'CIV323' was discovered and selected in August 2004 by the inventors as a flowering plant within the progeny of the stated cross in a controlled environment in S. Giuseppe di Comacchio (Ferrara), Italy.

Asexual reproduction of the new *Malus* variety by budding and grafting was first performed in September 2004 and in the following years in S. Giuseppe di Comacchio (Ferrara), Italy, and has demonstrated that the combination of characteristics as herein disclosed for the new *Malus* variety are firmly fixed and retained through successive generations of asexual reproduction. The new variety reproduces true to type.

When compared to plants of the parent varieties 'Galaxy' and 'A3-7', the claimed variety 'CIV323' differs primarily in the traits listed in table 1 below:

TABLE 1

| Comparison with Parent Varieties | | | |
|---|---|---|---|
| Characteristic in which the variety is different | State of expression of candidate variety | The female parent ('Galaxy') | The male parent ('A3-7') |
| Resistance to scab | Yes | No | Yes |
| Fruit: general shape | Cylindrical | Conic | Short —conic to round |
| Fruit: size | Small | Medium | Medium to large |
| Fruit: relative area of over color | Very large | Medium | Medium to large |
| Fruit: hue of over color | Purple red | Red | Medium red |

BRIEF DESCRIPTION OF THE INVENTION

The following traits have been repeatedly observed and are determined to be unique characteristics of 'CIV323' which in combination distinguish this apple tree as a new and distinct variety:

1. Intense red overcolor;
2. Scab resistance;
3. Medium vigor, open habit with short branches;
4. Good flavor; and
5. Good storage ability.

Of the commercial cultivars known to the inventors, the most similar in comparison to the new apple variety 'CIV323' is the variety 'CIVG198' (Patented; U.S. Plant Pat. No. 18,730). In comparison to the similar variety 'CIVG198', 'CIV323' differs primarily in the traits listed in table 2 below:

TABLE 2

| Comparison with Similar Variety | | | |
|---|---|---|---|
| Denomination of similar variety | Characteristic in which the similar variety is different | State of expression of similar variety | State of expression of candidate variety |
| 'CIVG198' | Fruit shape | Ellipsoid | Cylindrical |
| | Fruit size | Medium | Small |
| | Time of eating maturity | Late | Medium to late |

BRIEF DESCRIPTION OF THE DRAWINGS

The accompanying photographs illustrate the overall appearance of the new apple tree 'CIV323' showing the colors as true as is reasonably possible with color reproductions of this type. Color in the photographs may differ slightly from the color value cited in the detailed botanical description, which accurately describe the color of 'CIV323'.

DETAILED BOTANICAL DESCRIPTION

Figure 1:
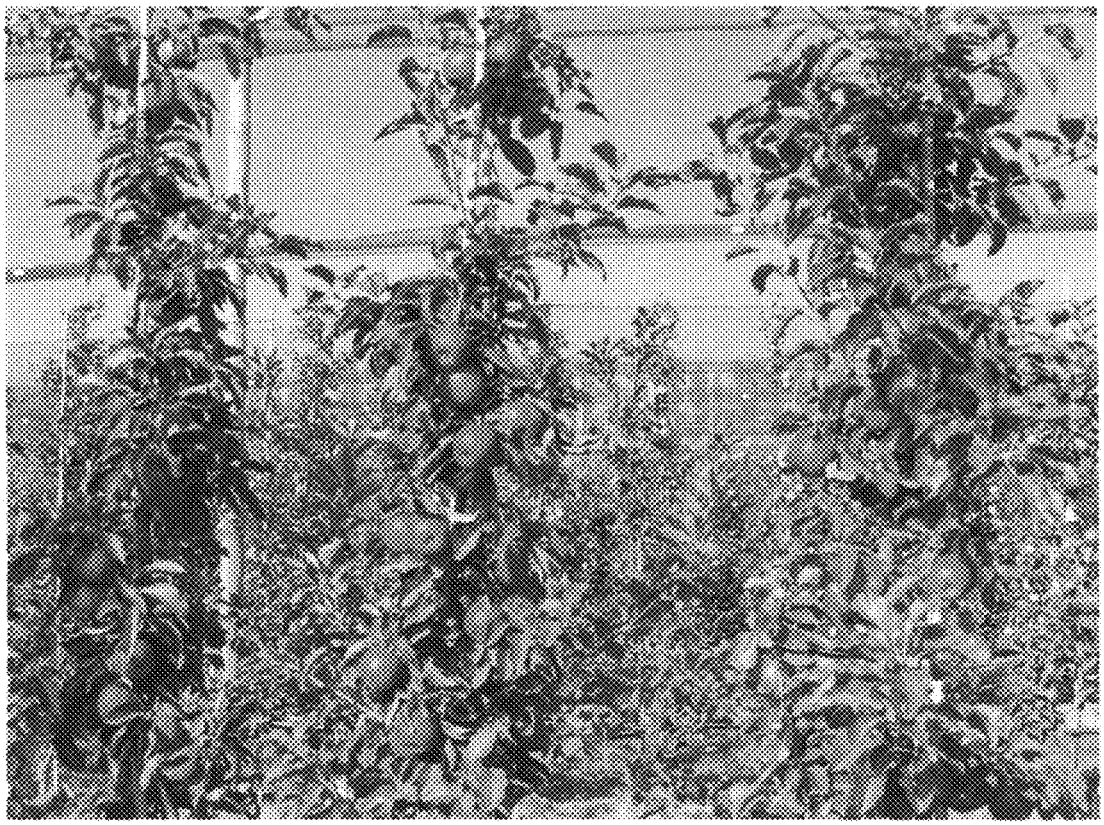
FIG. 1: illustrates the plant of 'CIV323'.
Figure 2:
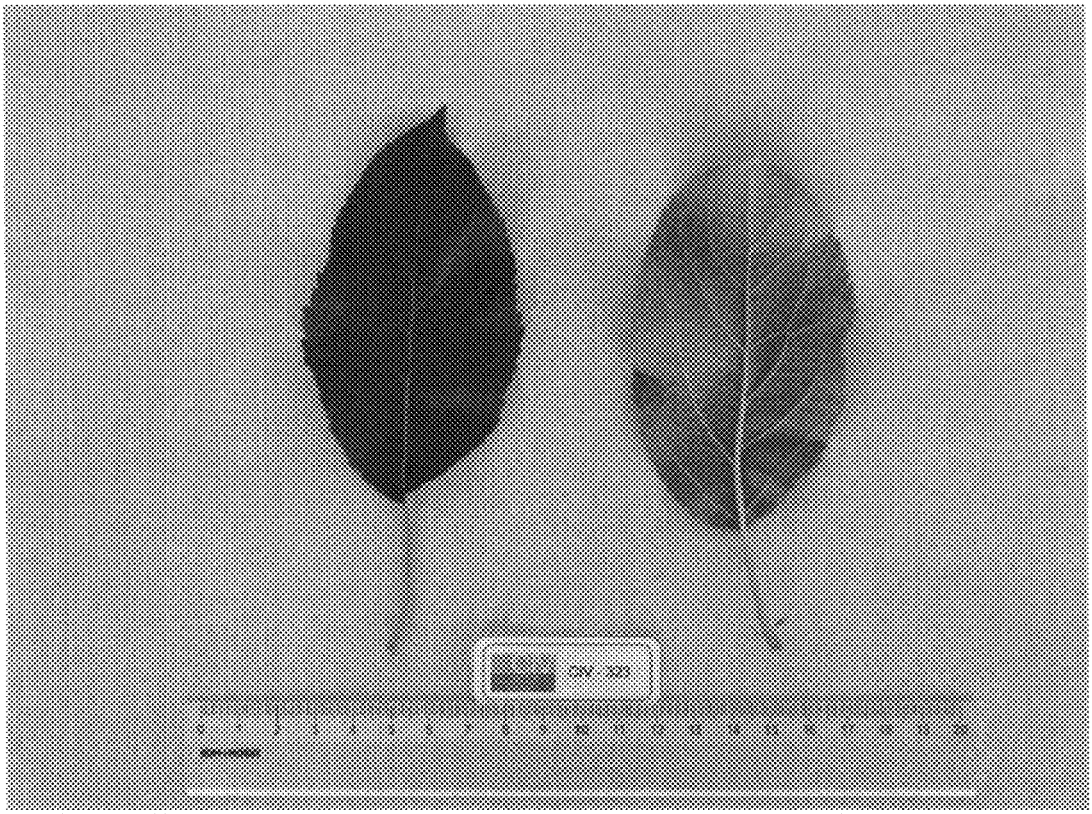
FIG. 2: illustrates the leaves of 'CIV323'.
Figure 3:
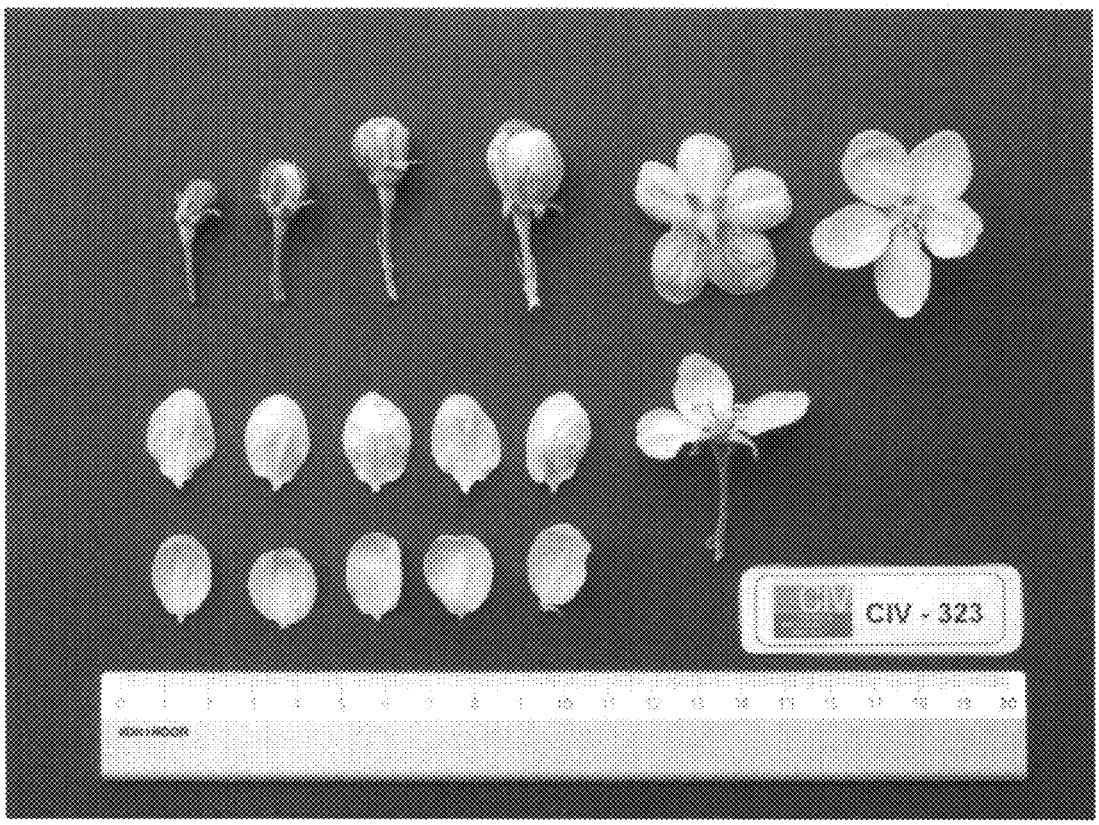
FIG. 3: illustrates the flowers of 'CIV323
Figure 4:
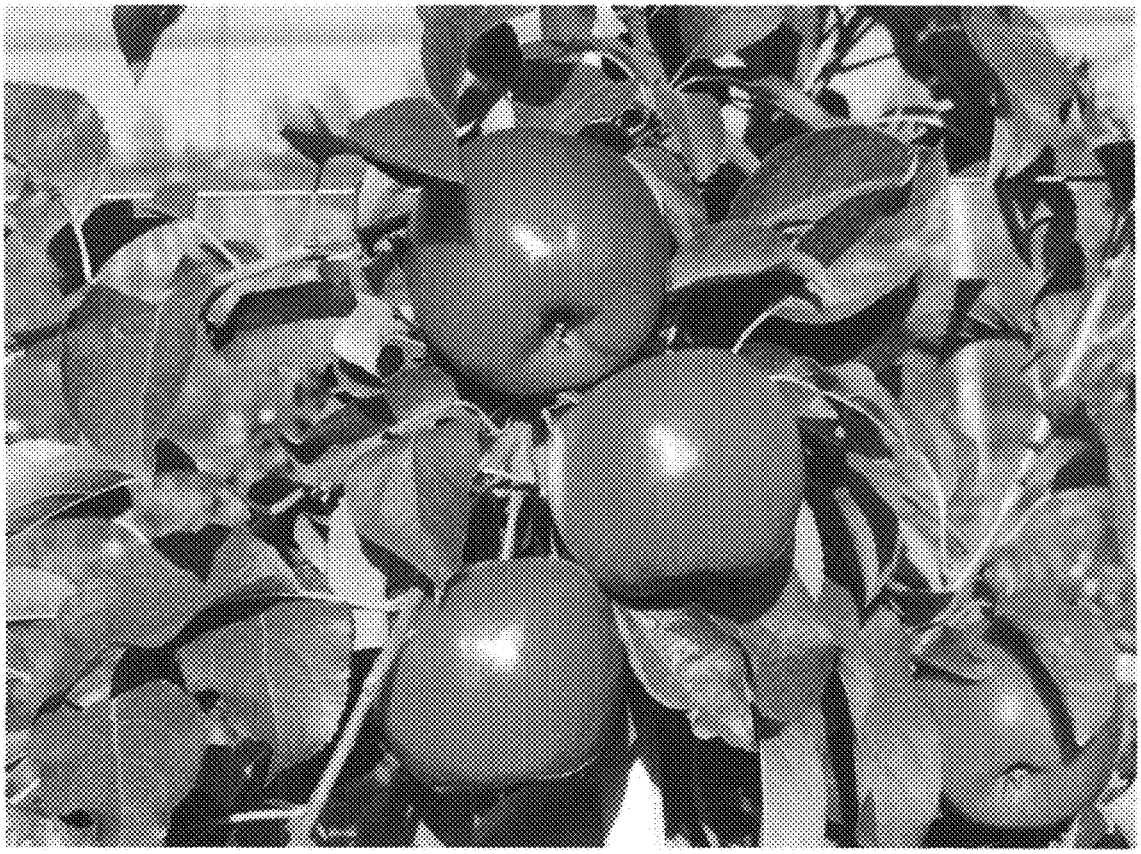
' and
FIG. 4: illustrates the fruits of 'CIV323'.

The new *Malus* variety 'CIV323' has not been observed under all possible environmental conditions. The phenotype of the new variety may vary with variations in environment such as temperature, light intensity, and day length without any change in the genotype of the plant.

The aforementioned photographs, together with the following observations, measurements and values describe the new *Malus* variety 'CIV323' as grown in the apple farm in S. Giuseppe di Comacchio (Ferrara), Italy, under conditions which closely approximate those generally used in commercial practice. The apple farm where 'CIV323' is grown is situated near the Adriatic sea (44°45' North, 12°11' East) and is zero (0) meters above sea level. The soil of the apple farm where 'CIV323' is grown is sandy, and the soil is treated with manure every year and irrigated with drip irrigation systems. The climate is temperate continental with high summer temperatures and low winter temperatures.

Unless otherwise stated, the detailed botanical description includes observations, measurements and values based on four (4) year old 'CIV323' trees that were grown in the apple farm in S. Giuseppe di Comacchio (Ferrara), Italy, from 2007 to 2010 All trees were of cropping maturity. Quantified measurements are expressed as an average of measurements taken from a number of individual trees of 'CIV323'. The measurements of any individual tree, or any group of trees, of the new variety may vary from the stated average.

Color references are made to The Royal Horticultural Society Colour Chart (R.H.S.), except where general colors of ordinary significance are used. Color values were taken under daylight conditions at approximately at 10:00 am in S. Giuseppe di Comacchio (Ferrara), Italy.

All trees of 'CIV323', insofar as they have been observed, have been identical in all the characteristics described below.

Classification:

*Botanical.*—*Malus domestica* Mill.

Parentage:

*Female parent.*—*Malus domestica* Mill. 'Galaxy' (unpatented).

*Male parent.*—*Malus domestica* Mill. 'A 3-7' (unpatented proprietary selection).

Propagation: Budding and grafting on M9 rootstock.

Tree:

*Age.*—Observed plants were four years old.

*Vigor.*—Medium vigor.

*Tree type.*—Ramified.

*Habit.*—Spreading, branches angle is typically 50 to 80 degrees from the vertical. stem.

*Density.*—Medium density to high.

*Cropping behavior.*—Precocious fruit bearing with high productivity.

*Type of bearing.*—On spur and long shoot.

*Production.*—$4^{th}$ year: 15 Kg.

*Size.*—Height: 2.8 m Spread: 1.10 m Trunk Diameter: about 36 mm as measured 20 cm above point of grafting.

*Surface texture.*—Smooth.

*Bark color.*—Greyed green RHS 197 B.

*Trunk lenticels.*—Overall Shape: elongated. Length: 1.9 mm. Width: 0.6 mm. Color: greyed orange RHS 164 A. Density: 1.5 to 2 per $cm^2$.

*Branches.*—Number per tree: about 25 at four (4) years. Length: Varies due to pyramidal shape of tree. At four (4) years, maximum of 70 cm to 90 cm; minimum of 25 cm to 40 cm. Diameter (at 3 years): About 10 mm to 12 mm. Surface texture: smooth. Color (at 3 years): greyed green, RHS 197 A. Internode length: About 2 cm to 4 cm. Internode diameter: About 9 mm in the middle of branches.

*Branches lenticels*.—Overall Shape: elongated. Length: 1.3 mm. Width: 0.27 mm. Color: greyed orange RHS 164 B. Density: About 2 to 3 per $cm^2$.

Leaves:

*Arrangement*.—Alternate, simple, petiolated.

*Lamina*.—Size: Length (4 year old): average 105.6 mm (from $3^{rd}$ to $5^{th}$ fully expanded leaf). Width (4 year old): average 57.6 mm (from $3^{rd}$ to $5^{th}$ fully expanded leaf). Length/width ratio: 1.8. Overall Shape: elliptic. Base shape: broad. Apex shape: acuminate. Margin: biserrate. Pubescence: absent on upper surface and weak pubescent on lower surface. Attitude in relation to shoot: outwards. Color (mature leaves): green RHS 147 A on the upper side and 147 B underside.

*Venation*.—Type: prominent pinnate venation from a midrib to the edge. Color: green RHS 146 C.

*Petiole*.—Length: about 33 mm. Diameter: 1.7 to 2.0 mm. Texture: hairy. Color: yellow green RHS 146 B with anthocyanin coloration localized at the base RHS 59 B red purple group.

*Stipule*.—Description: present. Small on the leaves, carried by old branches and spur. On one year old shoots the leaves are stipule adnate, grown together; length 10-12 mm, width 1.5-2.5 mm.

Spur:

*Present*.—On 2-3 year old shoots.

*Distance between each spur*.—On the two-three year old branches, the distance is about 20 mm to 30 mm.

*Number of fruit per spur*.—4 to 5 without thinning.

Flowers:

*Blooming time*.—Full bloom on April $5^{th}$ in S. Giuseppe di Comacchio (Ferrara) in year 2012.

*Blooming period*.—10 to 12 days.

*Fragrance*.—Typical of Rosaceae; the intensity is medium.

*Type*.—Corymb.

*Number of flowers per corymb*.—5 to 6.

*Flower size*.—Diameter: about 41 mm. Flower depth (height of the corolla): about 9 to 11 mm, measured when the flowers are fully open. Flower color: Primarily, white, RHS 155 B with shades of red-purple, RHS 63D when petals are fully opened. On the undersides of petals there are shades of red-purple RHS 72C. In the balloon stage the color is red-purple RHS 74 B.

*Buds*.—Number of buds per spur: typically one on each spur. Shape: pointed. Length: about 9.0 mm. Width: about 4.0 mm. Color: brown RHS 166 A with hairy surface.

*Petals*.—Arrangement: intermediate. Number per flower: typically five (5). Length: average 21 mm. Width: average 15 mm. Length/width ratio: 1.6. Overall shape: ovate. Apex shape: obtuse. Base shape: rounded with claw. Texture: smooth. Margin: entire. Color (upper surface): RHS 69 D with shade red-purple RHS 63 D. Color (lower surface): RHS 69 D with shade red-purple RHS 72 C.

*Sepals*.—Number per flower: five (5). Length: average 8 mm. Width: average 3 mm. Length/width ratio: 2.6. Overall shape: lanceolate. Apex shape: acute. Texture: hairy. Margin: entire. Color: green RHS 138 A on upper surface and RHS 138 B lower surface.

*Pedicel*.—Length: average 25 mm. Diameter: about 1.5 mm in the midle. Texture: hairy. Color: green, RHS 138 A.

Fruit:

*Keeping quality*.—The fruits has a long shelf life, up to two weeks without loosing firmness and juiciness.

*Maturity when described*.—Ripe for eating.

*Maturity period after full bloom*.—About 136 days in S. Giuseppe di Comacchio (Ferrara) Italy in 2012.

*Date of first and last pickings*.—About 23 August and 29 August in S.Giuseppe di Comacchio (Ferrara) Italy in year 2012.

*General shape*.—Cylindrical.

*Average weight*.—175.7 g.

*Fruit size*.—Average height: 68.4 mm. Average diameter (at widest point): 71 mm.

*Position of maximum diameter*.—In the middle of fruit.

*Height/diameter ratio*.—0.96.

*Stem*.—Length: average 26.7 mm. Diameter: average 2.06 mm. Color: yellow green group RHS 144 A.

*Stalk cavity*.—Depth: average 14.6 mm. Width: average 32.6 mm.

*Eye basin*.—Aperture of eye: partly open. Depth: average 8.9 mm. Width: average 30.5 mm. Crowning at calyx end: moderate. Position of sepals: erect. Calyx tube: "V" form.

*Skin*.—Thickness: medium. Texture: smooth. Bloom: weak. Greasiness: absent. Firmness (at picking time): 8 to 9 $kg/cm^2$. Overcolor color: red RHS 47 A. Percentage of skin surface with overcolor color: very large. Pattern of overcolor: solid flush only. Intensity of overcolor: dark. Ground color: yellow orange RHS 18 A.

*Skin lenticels*.—Shape: round or slightly elongated. Length: about 0.43 mm. Width: about 0.42 mm. Color: greyed orange RHS 163 C. Density: about 3.8 per $cm^2$ in the central area of the surface of fruit. The number of lenticels increases in a direction toward the hollow of the calyx and the size of the lenticels decreases.

*Flesh*.—Color: yellow RHS 18 D. Texture: fine. Tipe of flesh: crisp and juicy. Firmness: firm. Aroma: intense. Eating quality: the flavour is good, with high acid level a good content of sugar. Sugar content (at picking time): 13.5° to 14.0° Brix. Acidity/Starch (at picking time): Acidity: 8.0 to 9.5 g/l Malic acid/starch: 2.5-3. Laimburg scale 1 to 5.

*Core*.—Symmetry of core: asymmetric. Distinctness of core lines: not very evident. Locules: Number (per fruit): 5 (five). Length: average 8.0 mm. Width: average 3.5 mm. Form: fully open.

Seeds:

*Number per fruit*.—8 to 10.

*Number per locule*.—1 or 2.

*Shape*.—Elliptic, elongated and pointed.

*Length*.—Average 9.0 mm.

*Width*.—Average 5.2 mm.

*Color*.—Brown RHS 166 A.

Reproductive organs:

*Androecium*.—Stamens: Number per flower: about 18-20. Length: average 8.65 mm. Filament: Length: about 7.4 mm. Color: green-white RHS 157 C. Anther: Shape: ovoid, flat in the center. Length: about 2 mm. Diameter: about 1.5 mm. Color: yellow, RHS 8 C.

*Pollen*.—Amount: abundant. Color: yellow RHS 13 C. Requirements: the crab apple *Malus* 'Evereste' is a good pollinator.

*Gynoecium*.—Stigma: Shape: funnel shape with receptive surface on top. Length: 0.9 mm. Width: 0.4 mm. Color: Green RHS 145 A. Style: Number per flower: 5 (Five). Length: about 9.0 mm. Width: about 0.3 mm. Color: yellow green, RHS 145 C. Ovary: Length: about 3.0 mm. Width: about 3.0 mm. Color: green RHS 145 B.

*Use*.—Fresh market.

*Sensitivity to disease/pests*.—The variety 'CIV323' is resistant to scab.

*Winter hardiness*.—Tolerance to temperatures of −12° C. without observed damage to wood and buds of dormant apple trees; but open flowers and young fruits are killed by exposure to −3° C. to −5° C., depending on the length of exposure.

*Drought/heat tolerance*.—Good tolerance to heat, up to 40° C., growth is limited by drought periods without irrigation.

*Shipping/storage characteristics*.—Good storability under ULO-conditions (1° C., 2% $O_2$, 2% $CO_2$) for up to six (6) months.

We claim:

1. A new and distinct *Malus domestica* Mill. apple tree named 'CIV323', substantially as illustrated and described herein.

* * * * *